United States Patent [19]

Nakao et al.

[11] Patent Number: 5,336,181
[45] Date of Patent: Aug. 9, 1994

[54] ANTICLOTTING DEVICE AND METHOD FOR USE WITH IV CATHETERS

[76] Inventors: Naomi L. Nakao, 303 E. 57th St., New York, N.Y. 10022; Peter J. Wilk, 185 W. End Ave., New York, N.Y. 10023; John V. Mizzi, 30 Cramer Rd., R.F.D. #3, Poughkeepsie, N.Y. 12603

[21] Appl. No.: 875,455

[22] Filed: Apr. 29, 1992

Related U.S. Application Data

[63] Continuation-in-part of Ser. No. 836,768, Feb. 18, 1992, Pat. No. 5,195,967.

[51] Int. Cl.⁵ .............................................. A61M 5/00
[52] U.S. Cl. ................................. 604/83; 604/65; 128/DIG. 12
[58] Field of Search ........................... 604/65–67, 604/80–86, 151, 266, 268, 269; 128/DIG. 12, DIG. 13

[56] References Cited

U.S. PATENT DOCUMENTS

| | | | |
|---|---|---|---|
| 3,797,486 | 3/1974 | Shaps | 604/93 |
| 3,916,892 | 11/1975 | Latham, Jr. | |
| 3,965,896 | 6/1976 | Swank | |
| 4,094,318 | 6/1978 | Burke et al. | 604/81 |
| 4,137,915 | 2/1979 | Kamen | 128/DIG. 13 |
| 4,237,881 | 12/1980 | Beigler et al. | 604/65 |
| 4,444,198 | 4/1984 | Petre | |
| 4,451,255 | 5/1984 | Bujan et al. | 604/81 |
| 4,464,172 | 8/1984 | Lichtenstein | 604/65 |
| 4,493,693 | 1/1985 | Bilstad et al. | |
| 4,534,764 | 8/1985 | Mittleman et al. | |
| 4,538,918 | 9/1985 | Mittleman | |
| 4,540,406 | 9/1985 | Miles | |
| 4,553,958 | 11/1985 | LeCocq | 604/67 |
| 4,576,592 | 3/1986 | Danby | 604/253 |
| 4,681,563 | 7/1987 | Deckert et al. | 128/DIG. 13 |
| 4,769,001 | 9/1988 | Prince | |
| 4,946,439 | 8/1990 | Eggers | 604/81 |
| 5,195,967 | 3/1993 | Nakao et al. | 604/83 |

FOREIGN PATENT DOCUMENTS

| | | | |
|---|---|---|---|
| 9211891 | 7/1992 | PCT Int'l Appl. | 604/269 |
| 2042091 | 9/1980 | United Kingdom | 128/DIG. 12 |

*Primary Examiner*—Ralph Lewis
*Attorney, Agent, or Firm*—R. Neil Sudol; Henry D. Coleman

[57] ABSTRACT

A method for use in an intravenous tube assembly comprises the steps of automatically monitoring liquid flow along a fluid flow path extending through an intravenous catheter to detect at least a partial cessation of flow along the fluid flow path and, upon detecting a diminution of liquid flow along the fluid flow path, automatically feeding an anticlotting agent to the fluid flow path. An assembly for implementing the method takes the form of a systolic actuator for dividing the fluid flow into successive aliquots which can be timed. The systolic actuator extracts energy from the fluid stream and monitors the stream via the extracted energy. Alternatively, a pressure device is operatively connected to the catheter for automatically detecting at least a partial cessation of liquid flow along a fluid flow path extending through the catheter. The assembly also includes a feeder mechanism operatively connected to the catheter and the sensing device for automatically feeding an anticlotting agent to the fluid flow path through the catheter upon a detection by the sensing device of a diminution of liquid flow along the fluid flow path and, more particularly, of intravenous liquid flow in a distal direction into a patient's circulatory system.

35 Claims, 4 Drawing Sheets

ANTICLOTTING DEVICE AND METHOD FOR USE WITH IV CATHETERS

CROSS-REFERENCE TO A RELATED APPLICATION

This application is a continuation-in-part of commonly owned application Ser. No. 836,768 filed Feb. 18, 1992 now U.S. Pat. No. 5,195,967.

BACKGROUND OF THE INVENTION

This invention relates to a technique and a related device for preventing the formation of blood clots in intravenous catheters.

In an intravenous feeding assembly, an intravenous catheter is inserted into a person's vein and connected at a proximal end to an intravenous tube extending from a liquid supply. Frequently, intravenous lines are lost because the monitoring personnel forget to change the infusion bag and a clot forms in the catheter. In patients who have accessible veins, the intravenous line has to be restarted by a physician or a nurse specialist. Precious moments can be lost while the physician or nurse specialist is being sought. During that time, the patient does not receive intravenous fluid and does not have an intravenous line.

In addition, there are a large number of cases in which no further veins are accessible. In such cases, another intravenous can be started only with great difficulty, for example, by having a surgeon cut into a vein. In this group of patients, the maintenance of an intravenous line is especially crucial.

Intravenous lines are particularly critical for certain kinds of patients. For example, after a myocardial infarction, a patient's myocardium is irritable and the patient can go into a life-threatening arhythmia such as ventricular fibrillation. During that time, if there is no available intravenous port, intravenous medication cannot be injected and the patient dies. Also, when the patient is in ventricular fibrillation, it is extremely difficult to obtain venous access because blood is not being efficiently pumped. The absence of an intravenous line in the patient at that time can be a direct cause of death.

Patients who are bleeding and are receiving blood represent another critical group. When the intravenous line becomes clotted and the line is lost, it is again difficult to obtain venous access. Such a patient can bleed to death or exanguinate, if there is no readily available intravenous line.

Another critical group is patients who have a severe, life-threatening infection requiring the continuous or continual supply of antibiotics. In such cases, where the intravenous line is clotted and a physician or nurse specialist cannot be found, the patient can die.

In yet another critical group, the patients have a pulmonary embolus and require continuous heparinization. In such a patient, a clot in an intravenous line causing an interruption in the heparin flow of only a few minutes can result in the formation of another pulmonary embolism and instantaneous death.

Other consequences of interruption of intravenous lines include the prodding, bruising and pricking of unfortunate patients. For old people, especially, the restarting of intravenous lines is a constant source of pain and suffering.

Devices are known which generate an alarm, e.g., an audible signal, upon the exhaustion of an intravenous supply or the formation of a blockage in the intravenous flow path. Such devices typically include a photoelectric drip sensor which monitors fluid flow in an intravenous line. Upon a cessation of fluid flow, the photoelectric sensor triggers the alarm. It is to be noted that care-takers are frequently unavailable at the time an intravenous supply runs out and an alarm sounds.

Heparin is an anticlotting compound and is provided in catheters which are inserted intravenously for enabling periodic access to a patient's blood or circulatory system. Inasmuch as such catheters are closed at a proximal end, for example, by a self-sealing polymeric membrane, the heparin remains in the catheter owing to suction forces. Such a device is known as a heparin lock.

U.S. Pat. No. 5,195,967 discloses a method and apparatus for automatically activating or instituting a heparin lock upon an automatic detection of at least a partial cessation of fluid flow along an intravenous flow path. In one mechanically implemented embodiment, the apparatus is responsive to a pressure drop along the intravenous flow path at an intravenous catheter. However, it has been discovered that the pressure sensing approach is not easily adapted to all cases. Specifically, the catheter diameter and the intravenous flow rate, as well as the materials and design of the sensing components, must be delicately matched to ensure heparin lock activation upon a termination of intravenous flow due to exhaustion of an intravenous fluid supply.

OBJECTS OF THE INVENTION

An object of the present invention is to provide a method for reducing the incidence of blood clots forming in intravenous catheters.

Another object of the present invention is to provide an associated device for reducing the incidence of blood clots forming in intravenous catheters.

Another, more particular, object of the present invention is to provide an automatic anticlotting device, such as an automatic heparin lock.

A further particular object of the present invention is to provide a device for automatically sensing a diminution of liquid flow through an intravenous catheter and for automatically introducing heparin into the catheter upon detection of a diminution of liquid flow termination.

Other objects of the present invention will be apparent from the detailed descriptions and drawings included herein.

SUMMARY OF THE INVENTION

A method for use in an intravenous tube assembly comprises, in accordance with the present invention, the steps (a) automatically dividing, into a succession of consecutive aliquots of liquid, a liquid flow along a fluid flow path extending through an intravenous catheter, (b) automatically timing the consecutive aliquots to detect at least a partial cessation of liquid flow along the fluid flow path, and (c) upon detecting at least a partial cessation of liquid flow along the fluid flow path, automatically feeding an anticlotting agent to the fluid flow path.

Pursuant to a specific embodiment of the present invention, the method may further comprise the steps of (d) automatically sensing the aliquots during motion thereof along the fluid flow path and (e) generating an electrical signal upon the sensing of each consecutive aliquot. In this embodiment of the invention, the aliquots constitute drops of liquid and the step of automatically sensing may particularly include the step of photoelectrically monitoring the drops. The timing of the drops may be accomplished electronically.

Pursuant to a particular feature of the present invention, feeding of the anticlotting agent to the fluid flow path is implemented by heating a meltable substance in a valve to open a valve member.

In accordance with another embodiment of the present invention, the liquid flow is divided by operating a fluid flow engine in the fluid flow path. The timing of the successive aliquots of liquid is accomplished by monitoring the operating cycle of the fluid flow engine.

According to a particular feature of the present invention, the fluid flow engine is a systolic actuator having a pair of chambers. Then the dividing of the liquid flow is implemented by alternately filling and emptying the chambers.

Pursuant to another feature of the present invention, monitoring the operating cycle of the flow engine includes the step of using energy from the engine to pressurize a collapsible pouch. The feeding of the anticlotting agent to the flow path then includes the step of collapsing the pouch in response to a delay in the operation of the engine occasioned by a diminution of fluid flow along the flow path. The feeding of the anticlotting agent further includes the step of opening a pressurized reservoir of the anticlotting agent in response to the step of collapsing.

The method in accordance with the present invention may further comprise the step of automatically blocking communication between the catheter and an intravenous tube connected to the catheter. The blocking is exemplarily attained by operating a one-way blocking valve, for example, a floating ball type valve.

A device for use with an intravenous catheter comprises, in accordance with the present invention, a dividing mechanism operatively connectable to the catheter for automatically dividing, into a succession of consecutive aliquots of liquid, a liquid flow along a fluid flow path extending through the catheter. A timing component is operatively connected to the dividing mechanism for automatically timing the consecutive aliquots to detect at least a partial cessation of liquid flow along the fluid flow path. A feeder is operatively connected to the timing component and couplable to the catheter for automatically feeding an anticlotting agent to the fluid flow path upon a detection by the timing component of at least a partial cessation of liquid flow along the fluid flow path.

According to another feature of the present invention, the dividing mechanism includes a fluid flow engine, while the timing component includes a monitor operatively connected to the engine for monitoring an operating cycle thereof.

Preferably, the fluid flow engine is a systolic actuator having a pair of chambers, and the dividing mechanism includes a valve or other subunit operatively connected to the actuator for filling a first chamber with liquid from the fluid flow path while emptying a second chamber of liquid during a half cycle of operation of the systolic actuator. The valve is preferably a reversing valve which changes the direction of fluid flow into and out of the systolic chambers at the termination of each half cycle of engine operation.

According to an additional feature of the present invention, the timer or monitor includes a collapsible pouch having an air outlet. The systolic actuator includes a pressurization component operatively connected to the pouch for supplying a pressurizing air charge to the pouch during a cycle and preferably during each half cycle of operation of the systolic actuator.

Pursuant to another feature of the present invention, the feeder includes an element operatively connected to the pouch for opening communication between the fluid flow path and a storage chamber containing the anticlotting agent. The opening element may be provided as a sharpened point on a spring between two legs of which the collapsible pouch is disposed. The pointed element on the spring punctures a closure member to open a storage chamber upon a collapse of the pouch. The rupture of the closure member (e.g., a foil panel) enables pressurized anticlotting agent such as heparin to escape the storage chamber into the fluid flow path.

The pressurization of the pouch in response to the fluid flow preferably includes a pump such as a bellows operatively coupled to the systolic chambers for providing air to the pouch in response to periodic filling and emptying of the chambers. The bellows is pumped by a pivotably mounted bar disposed between the chambers of the systolic actuator. A flexible leaf spring is connected to an end of the bar and periodically swats the bellows to provide a puff of air to the collapsible pouch.

A method for use in an intravenous tube assembly comprises, in accordance with another conceptualization of the present invention, the steps of (i) automatically accumulating energy from a flow of intravenous liquid along a fluid flow path extending through an intravenous catheter, (ii) automatically monitoring the rate of energy accumulation to detect at least a partial cessation of fluid flow along the flow path, and (iii) upon detecting at least a partial cessation of liquid flow along the fluid flow path, automatically feeding an anticlotting agent to the fluid flow path.

The accumulation of flow energy includes the step of supplying the energy to an energy storage device. Pursuant to another feature of the present invention, this method further comprises the step of automatically releasing accumulated energy from the energy storage device.

Pursuant to another feature of the present invention, the energy storage device is a spring.

The step of accumulating energy from an intravenous fluid flow preferably includes the step of driving a fluid flow engine disposed in the fluid flow path. The accumulated energy is fed to an energy storage device. More preferably, the engine is a systolic actuator having a pair of chambers, the engine being driven by an alternate filling and emptying of the chambers.

A device for use with an intravenous catheter comprises, in accordance with the present invention, an energy accumulator operatively connectable to the catheter for automatically accumulating energy from a flow of intravenous liquid along a fluid flow path extending through the catheter. A monitor is operatively connected to the energy accumulator for automatically monitoring the rate of energy accumulation to detect at least a partial cessation of fluid flow along the flow path. A feeder is operatively linked to the monitor and is couplable to the catheter for automatically feeding an anticlotting agent to the fluid flow path upon a detection by the monitor of at least a partial cessation of liquid flow along the fluid flow path.

Pursuant to a further feature of the present invention, the monitor includes a spring and a mechanism operatively coupled with the spring for maintaining the spring in an energy bearing configuration. That maintenance mechanism preferably includes a collapsible pouch disposed between legs of the spring. The monitor further comprises means for pressurizing the pouch in response to liquid flow along the fluid flow path.

According to an additional feature of the present invention, the feeder includes an opening mechanism operatively connected to the pouch for opening communication between the fluid flow path and a storage chamber containing the anticlotting agent. Where the feeder includes a spring member bearing the opening element in the form of a pointed portion of the spring member, the pouch is disposed between two legs of the spring member, whereby the pointed spring portion punctures a closure member to open the storage chamber upon a collapse of the pouch.

Pursuant to another feature of the present invention, the pouch is provided with an outlet, whereby the pouch automatically depressurizes under pressure by the legs of the spring in the absence of pressurization.

According to yet another feature of the present invention, the energy accumulator includes a flow engine connectable to the flow path. Preferably, as discussed hereinabove, the flow engine is preferably a systolic actuator having a pair of chambers, the accumulator including a reversing valve operatively connected to the actuator for filling one of the chambers with liquid from the fluid flow path while emptying another of the chambers of liquid during a half cycle of operation of the systolic actuator.

Use of a device in accordance with the present invention serves to reduce the incidence of blood clots forming in intravenous catheters. In particular, a device in accordance with the present invention prevents a clot from forming in an intravenous catheter upon the exhausting of an intravenous liquid supply, whether saline solution, blood plasma or other liquid.

DETAILED DESCRIPTION

Figure 1:
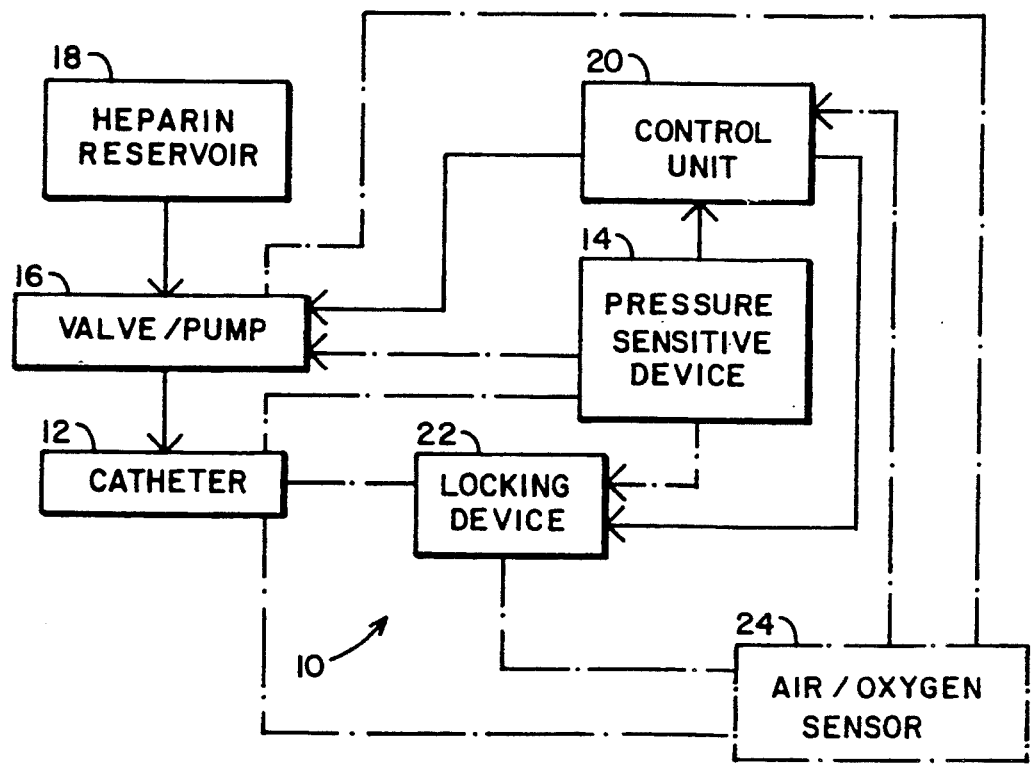
FIG. 1 is a block diagram of an electrically or mechanically implemented automatic heparin lock in accordance with the present invention.

As illustrated in FIG. 1, an automatic heparin lock device or assembly 10 connectable to a catheter 12 comprises a flow sensitive device 14 operatively connected to the catheter for acting in response to fluid flow along an intravenous path extending from a liquid supply (not shown) through the catheter. More particularly, flow sensitive device 14 detects, or is responsive to, a diminution in fluid flow which occurs upon either an exhaustion of fluid in the liquid supply or a blockage in the fluid flow path preventing or reducing the flow of fluid. In the former eventuality, the liquid stream is replaced by air along at least a portion of the flow path, which results in a pressure drop.

As discussed hereinafter with respect to specific embodiments illustrated in FIGS. 2 and 3, flow sensitive device 14 may be sensitive to pressure. Alternatively, as described below with reference to FIG. 5 and 6, flow sensitive device 14 may comprise a photoelectric drip sensor or a flow engine which monitors flow rather than pressure.

As further illustrated in FIG. 1, heparin lock or assembly 10 also comprises a valve or pump 16 which is disposed between a heparin reservoir 18, on the one hand, and catheter 12 or the fluid path through the catheter, on the other hand. Valve or pump 16 is operated by flow sensitive device 14 either directly or via a control unit or logic circuit 20. Upon a detection by flow sensitive device 14 of a pressure drop concomitant with a diminution of intravenous liquid flow through catheter 12, valve or pump 16 is actuated to feed heparin from reservoir 18 to catheter 12 or, equivalently, to the intravenous path extending through the catheter.

Heparin lock or assembly 10 additionally comprises a locking device or mechanism 22 which functions to block communication between catheter 12 and an intravenous tube connected thereto. Locking device 22 is operatively connected to flow sensitive device 14 for operating in conjunction therewith or in response to signals transmitted directly from flow sensitive device 14 or indirectly therefrom via control unit 20.

As an alternative to flow sensitive device 14, an air or oxygen sensor 24 may be operatively connected to valve 16, either directly or via control unit 20, and to catheter 12. Upon detecting air or, more specifically, oxygen along the fluid path extending through the catheter, sensor 24 acts to actuate valve 16 to transfer heparin from reservoir 18 to the intravenous path extending through catheter 12. In a conventional intravenous delivery system including an intravenous line (not shown in FIG. 1) extending to catheter 12 from a liquid supply bag (not shown), sensor 24 is connected to the intravenous line above a flow-regulating throttle valve (not shown) for determining when the supply has been exhausted. Naturally, air or oxygen sensor 24 will be ineffective in the event there is a blockage in the intravenous flow path.

Figure 2:
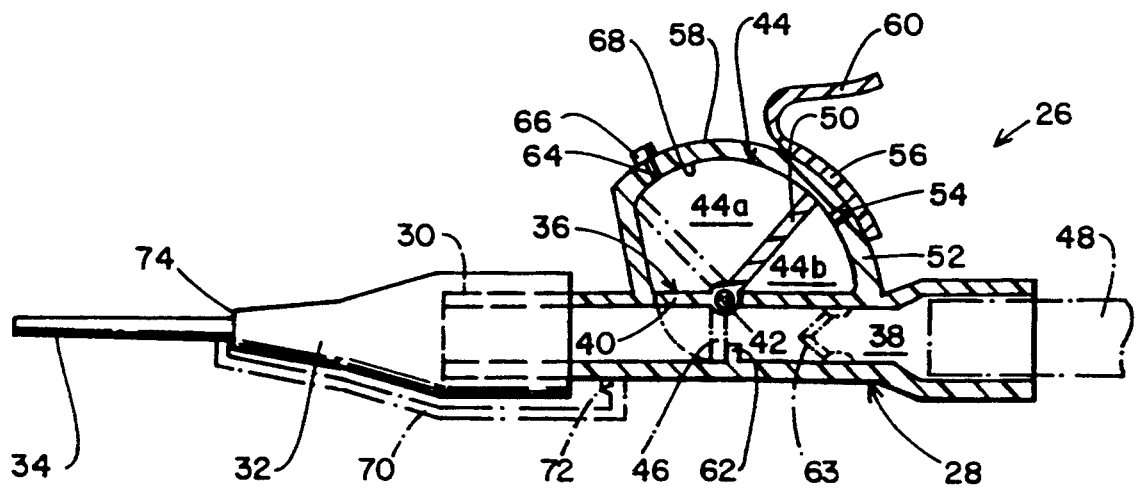
FIG. 2 is a schematic cross-sectional longitudinal view of a mechanical heparin lock which may be used to specifically implement the heparin lock of FIG. 1.

As illustrated in FIG. 2, a mechanically implemented automatic heparin lock 26 includes a body member 28 having a distal end 30 insertable into the proximal end of a catheter body or holder 32, thereby connecting the heparin lock 26 to a catheter 34. Body member 28 includes a pressure monitoring or detecting device 36 which senses or is responsive to a diminution or partial cessation of liquid flow through a main channel 38 of body member 28. Channel 38 defines a fluid flow path which extends through catheter 34 and catheter body 32 in a distal direction into a patient's circulatory system (not illustrated).

Pressure monitoring device 36 includes a door or valve element 40 rotatably hinged to body member 28 at a pivot pin 42. In a pre-use configuration, door 40 closes an ancillary chamber 44 in body member 28 and thereby prevents communication between that chamber and channel 38. Upon an actuation of pressure monitoring device 36, in response to a drop in fluid pressure in channel 38, door 40 rotates in a counter-clockwise direction about pivot pin 42 to a blocking position illustrated in dot-dash lines at 46. In blocking position 46, door 40 extends transversely across channel 38 and serves to block communication between catheter body 32 and catheter 34, on the one hand, and an intravenous tube 48, on the other hand. Tube 48 is connected to catheter 34 via heparin lock member 28 prior to the commencement of an intravenous feeding or transfer operation.

Heparin lock 26 further comprises a rotary piston element 50 which is rigid with door 40 and rotatably attached to body member 28 via pivot pin 42. Rotary piston element 50 is disposed in chamber 44 and partitions that chamber into a first portion 44a and a second portion 44b. First chamber portion 44a contains a predetermined aliquot of an anticlotting agent such as heparin (not illustrated), while second chamber 44b serves in the maintenance of a suction hold on piston element 50 prior to installation of heparin lock 26, i.e., prior to a coupling of body member 28 to catheter body 32 and intravenous tube 48 and an initiation of liquid flow along a fluid flow path extending through intravenous tube 48, channel 38 of body member 26, and catheter 34. To that end, a wall 52 of main body 28 is provided with an aperture 54 extending to second chamber portion 44b.

Prior to utilization of heparin lock 26 in conjunction with intravenous catheter 34, a closure strip 56 is adhesively attached to an outer surface 58 of wall 52 to close aperture 54 and thereby maintain a suction force on piston element 50 which prevents the rotation of that element and concomitantly door 40 about pin 42 and locks the aliquot of heparin in first chamber portion 44a. Closure strip 56 is provided with a pull tab 60 by which a user removes the strip from outer surface 58 and thereby opens aperture 54 upon a connection of intravenous tube 48 and body member 28 to catheter body 32 and a commencement of a liquid flow along a fluid flow path extending through the intravenous tube, channel 38 of body member 26, and catheter 34.

During a flow of intravenous liquid along the feed path through intravenous tube 48, channel 38 of body member 26, and catheter 34, the fluid pressure in channel 38 pushes against door 40, keeping the door closed and the heparin charge contained in chamber portion 44a. Upon a pressure drop in channel 38, which corresponds to a diminution of intravenous liquid flow, door 40 is pushed open and into blocking position 46 by the heparin in chamber portion 44a and by rotary piston 50. To facilitate this rotation of door 40 and the feed or injection of the heparin charge from chamber portion 44a into channel 38 and towards catheter 34, pressure monitoring device 36 may be provided with a spring element (not shown) which tends to rotate door 40 towards blocking position 46. Of course, the rotary force exerted by this biasing spring is not so great as to open door 40 and discharge the heparin while intravenous liquid is flowing through channel 38 of body member 26. It is to be noted that the biasing spring functions, together with door 40, as a sensor or detector of fluid pressure in channel 38. The biasing spring additionally functions with door 40 to block communication between catheter 34 and intravenous tube 48, upon a detection of a drop in pressure signaling a partial cessation or diminution of liquid flow through channel 38. The biasing spring cooperates with rotary piston element 50 to feed or inject a heparin charge into channel 38 and accordingly into the fluid flow path extending to catheter 34.

Body member 28 is provided along channel 38 with a stop 62 which arrests the counterclockwise motion of door 40 and piston element 50 and defines the channel blocking position 46 of door 40. In addition, body member 28 may be provided along channel 38 with a one-way valve 63 which together with door 40 serves to prevent a back-flow of heparin into tube 48.

Body member 28 may also be provided with a bore 64 extending through wall 52 to chamber portion 44a for enabling the loading of a heparin charge into that chamber portion. Bore 64 is closed or sealed by a plug 66.

During a feeding of heparin from chamber portion 44a to channel 38 by piston element 50, an outer end of that element moves in a sealing engagement against a correspondingly profiled inner surface 68 of wall 52.

Heparin lock body member 28 may be provided with an optional latch 70 pivotably mounted to body member 28 at 72 for swinging around catheter body 32 to engage a distal end 74 thereof in a releasable snap lock fit. Latch 70 serves to prevent or inhibit an untimely disengagement of body member 28 and catheter body 32.

Figure 3:
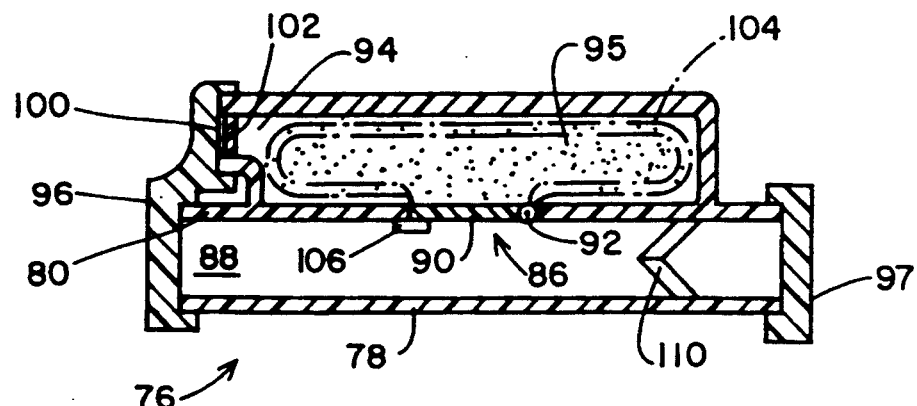
FIG. 3 is a schematic cross-sectional longitudinal view of another mechanical heparin lock.

As illustrated in FIG. 3, a mechanically implemented automatic heparin lock 76 includes a body member 78 having a distal end 80 insertable into the proximal end of a catheter body or holder 82 (FIGS. 4A–4D), thereby connecting the heparin lock 76 to a catheter (not shown). Body member 78 includes a pressure monitoring or detecting device 86 which senses or is responsive to a diminution or partial cessation of liquid flow through a main channel 88 of body member 78. Channel 88 defines a fluid flow path which extends through the catheter and catheter body 82 in a distal direction into a patient's circulatory system (not illustrated).

Pressure monitoring device 86 includes a door or valve element 90 rotatably hinged to body member 78 at a pivot pin 92. In a pre-use configuration, door 90 closes an ancillary chamber 94 in body member 78 and thereby prevents communication between that chamber and channel 88. Upon an actuation of pressure monitoring device 86, in response to a drop in fluid pressure in channel 88, door 90 rotates in a counter-clockwise direction about pivot pin 92 enable the flow of an aliquot of heparin 95 from chamber 94 into channel 88.

Heparin lock 76 further comprises a pair of end caps 96 and 97 disposed on opposite ends of body member 78 to close channel 88 and thereby maintain the channel in a sterile condition. Prior to the commencement of an intravenous feeding or transfer operation, end caps 96 and 97 are removed and an intravenous tube 98 (FIGS. 4A–4D) connected to catheter 84 via heparin lock member 78, as illustrated in FIG. 4A.

The removal of end cap 96 simultaneously opens a breather aperture 100 which may be provided with a semipermeable membrane 102 which permits the passage of air but not a liquid such as heparin. Alternatively or additionally, a balloon 104 is provided inside chamber 94 for containing the heparin and pressing it through door 90 upon a falling of the fluid pressure in channel 88 below a predetermined threshold value. Breather membrane 102 and balloon 104 each serve as a barrier which prevent the leakage or flow of heparin out through breather aperture 100.

Prior to use of heparin lock 76, door 90 is held closed by a glue layer or spot 106 of a water-dispersible material such as sugar. Consequently, neither pressure due to balloon 104 nor the internal pressure of the heparin, released upon a removal of end cap 96 and an opening of breather aperture 100, will result in an immediate opening of door 90 and a flow of heparin from chamber 94 into channel 88.

Figure 4A:
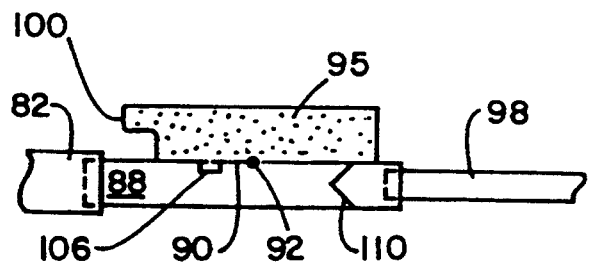
FIGS. 4A–4D are schematic cross-sectional views showing different stages in the utilization and operation of the automatic heparin lock of FIG. 3.
Figure 4B:
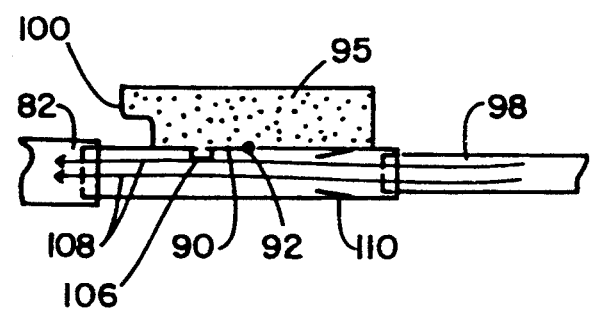
Figure 4C:
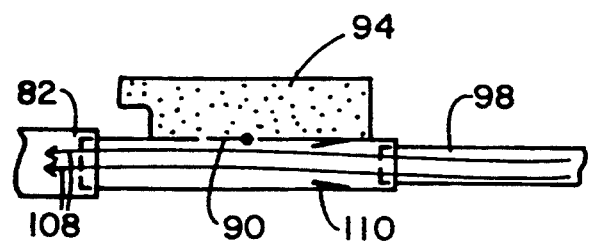
Figure 4D:
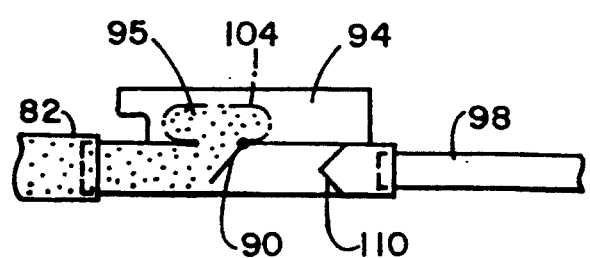

FIG. 4A shows heparin lock 76 after a removal of end caps 96 and 97 and a connection of intravenous tube 98 and catheter body 82 to the heparin lock body member 78, while FIG. 4B shows the heparin lock 76 just after intravenous fluid has begun to flow through channel 88, as indicated by flow arrows 108. After a period of time determined largely by the composition of the water dispersible or dissolvable material of layer or spot 106, that layer or spot disappears, as shown in FIG. 4C. Subsequently, during a continued flow of intravenous liquid along the feed path through intravenous tube 98, channel 88 of body member 76, and catheter body 82, the fluid pressure in channel 88 pushes against door 90, keeping the door closed and the heparin charge contained in chamber 94. Later, upon a pressure drop in channel 88, corresponding to a diminution of intravenous liquid flow, door 90 is pushed outwardly into channel 88 (FIG. 4D) by the heparin in chamber 94 and, additionally or alternatively, by balloon 104.

To further facilitate this rotation of door 90 and the feed or injection of the heparin charge from chamber 94 into channel 88 and towards catheter/catheter body 82, pressure monitoring device 86 may be provided with a spring element (not shown) which tends to rotate door 90 in the counterclockwise direction, as illustrated in the drawing. The rotary force exerted by this biasing spring, by the pressure of the heparin and/or by balloon 104, is not so great as to open door 90 and discharge the heparin while intravenous liquid is flowing through channel 88 of body member 76.

Body member 78 may be provided along channel 88 with a one-way valve 110 which together with door 90 serves to prevent a back-flow of heparin into tube 98.

It is to be understood that catheters 34 and 82 are of small diameter and that the intravenous flow rate is relatively large, to provide enough pressure to maintain doors 46 and 90 closed when intravenous fluid is flowing and to provide, upon an exhaustion of the intravenous supply, a pressure drop sufficiently great to open the doors and thereby activate the respective mechanically implemented heparin locks.

Figure 5:
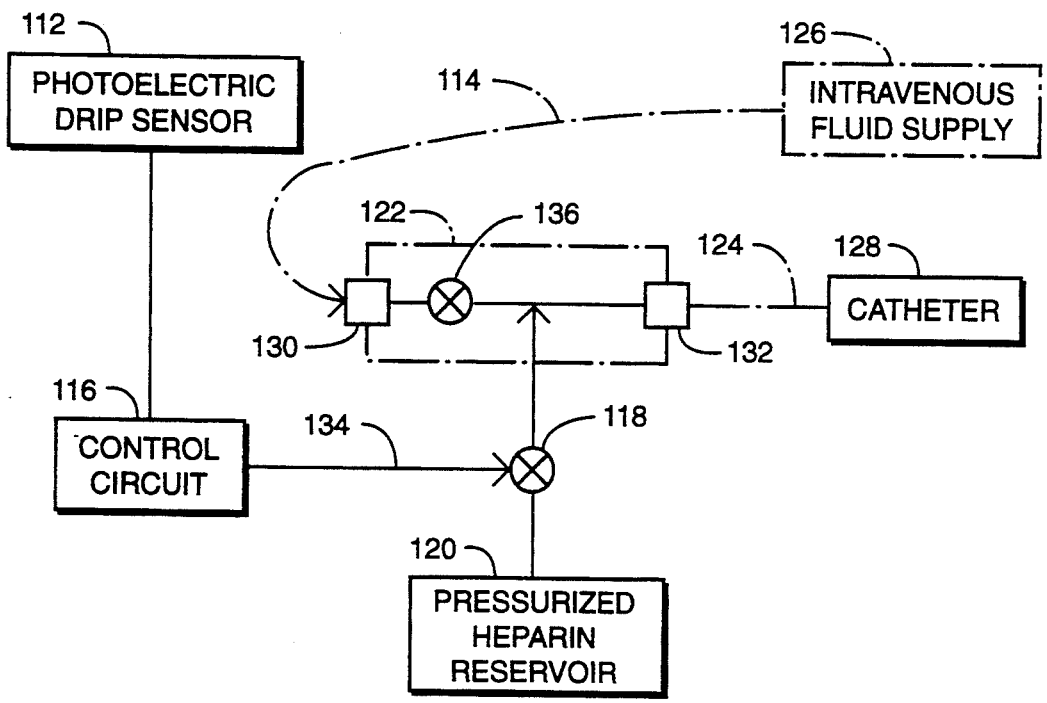
FIG. 5 is a block diagram of an automatic heparin lock with generally electrical actuating componentry, in accordance with the present invention.

As illustrated in FIG. 5, an automatic heparin lock comprises a photoelectric drip sensor 112 which is arranged disposed beside an intravenous flow line 114 for monitoring the flow of fluid therethrough. Photoelectric drip sensor 112 is connected to or incorporates a control circuit 116 which is operatively connected at an output to a valve device 118 for operating the valve to enable the flow of heparin from a pressurized reservoir 120 into a chamber 122 in a fluid flow path 124 extending from an intravenous fluid supply 126 along intravenous line 114 to an intravenous catheter 128. Chamber 122 is connected at an upstream side to intravenous line 114 via a coupling element 130 and at a downstream side to catheter 128 via another coupling element 132.

Photoelectric drip sensor 112 monitors successive aliquots or drops of liquid moving along the intravenous flow path, while control circuit 116 times the consecutive drops. Upon a detection by photoelectric drip sensor 112 and control circuit 116 of a diminution in fluid flow along flow path 124, i.e., upon a determination by control circuit 116 that the time between successive drops has exceeded a predetermined threshold, control circuit 116 transmits an electrical signal to valve device 118 for opening the valve to enable the injection of heparin from reservoir 120 into chamber 122.

Valve device 118 may be closed by a wax plug (not illustrated) surrounded by one or more turns of a resistance wire 134 connected to control circuit 116. The electrical signal from control circuit 116 increases the temperature within the turns of resistance wire 134. This increase of temperature in turn heats and melts the wax in valve device 118, thereby opening the valve. Any desired delay in the triggering of the heparin release may be designed into the lock of FIG. 5 by careful specification of the resistance of wire 134, the type of wax, and the heat conductivity of other components in valve device 118. A delay is desirable to give a caretaker an opportunity to reset the intravenous feed upon sensing a conventional alarm (not shown) connected to photoelectric drip sensor 12 via control circuit 116.

The automatic heparin lock of FIG. 5 further includes a one-way valve 136 for blocking the flow of heparin into intravenous line 114 from chamber 122 upon the release of the heparin from reservoir 120. Blocking valve 136 thus isolates the heparin infused area from intravenous line 114, concentrates the pressure pulse towards the patient, and also eliminates the chance of heparin dilution by intravenous solution diffusing into the heparin area from upstream.

Figure 6:
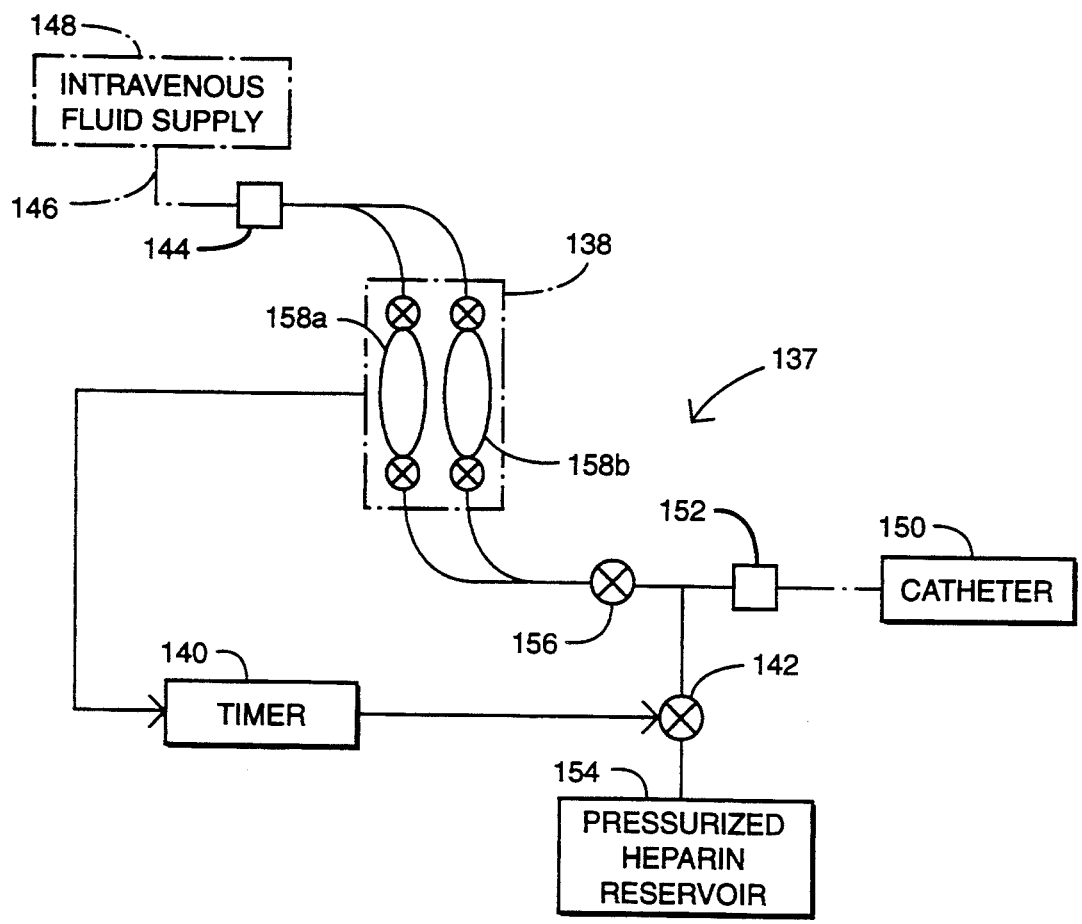
FIG. 6 is a block diagram of another automatic heparin lock which includes a flow sensitive or fluid engine, in accordance with the present invention.

As shown in FIG. 6, another automatic heparin lock 137 comprises a systolic actuator 138, a watchdog timer 140 and a mechanical heparin trigger 142. Systolic actuator 138 is connected via a coupling element 144 to an intravenous line 146 extending from a fluid or solution supply 148. Systolic actuator 138 functions to monitor flow by periodically accumulating and releasing flow so that the periodicity of the accumulation and release is directly related to the flow rate. Concomitantly, a steady flow to the patient is maintained.

Timer 140 is connected to systolic actuator 138 for detecting, in the action thereof, a slow down occasioned by a diminution or cessation of fluid flow along an intravenous flow path extending from supply 148 through line 146 and heparin lock 137 to a catheter 150. Catheter 150 is connected to heparin lock 137 via a coupling element 152. Upon detecting such a slow down, timer 140 induces mechanical heparin trigger 142 or valve to release heparin from a pressurized reservoir 154 into the fluid flow path between a one-way blocking valve 156 and coupling element 152.

Figure 7:
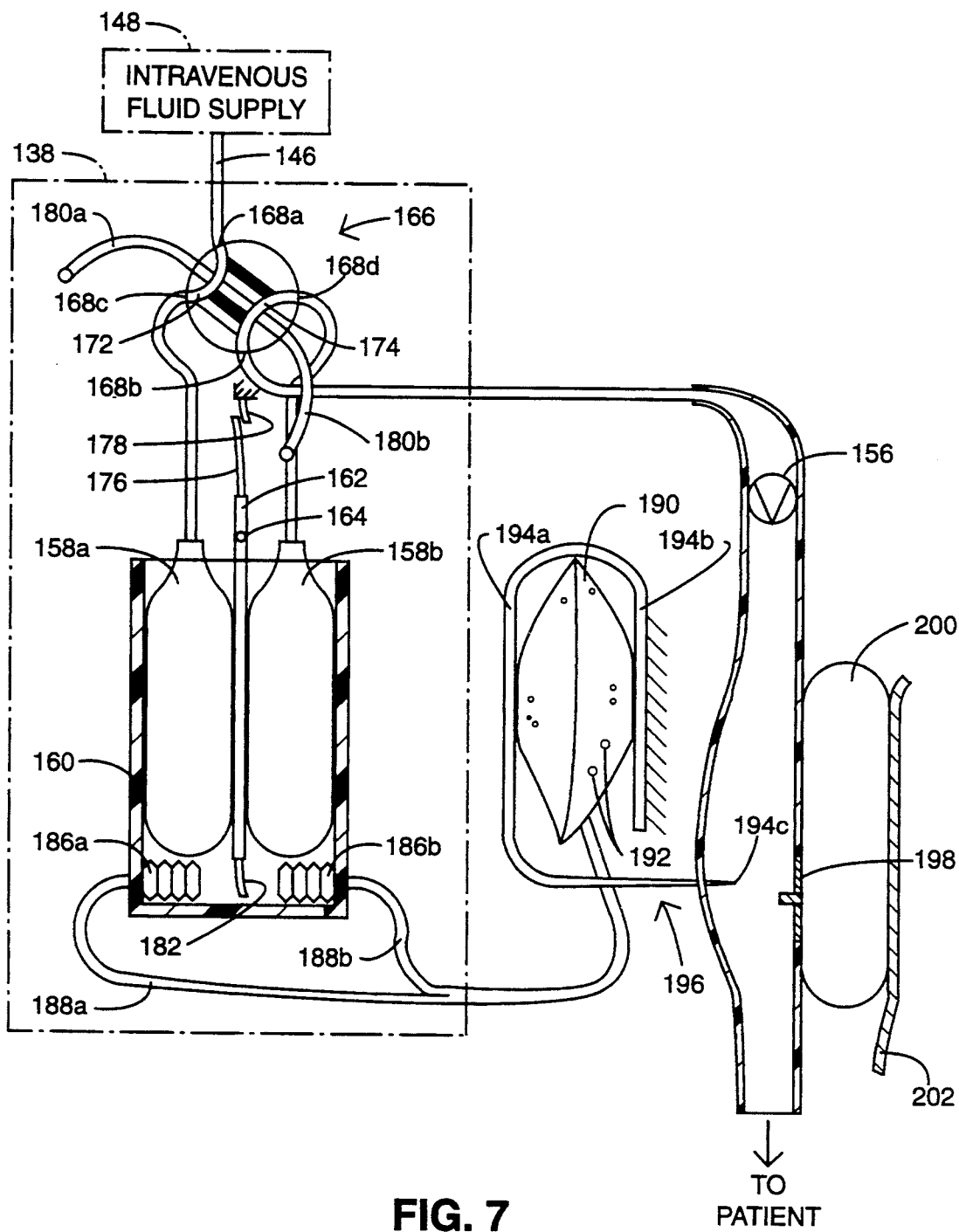
FIG. 7 is a more detailed diagram of the heparin lock of FIG. 6.

As depicted in FIGS. 6 and 7, systolic actuator 138 comprises a pair of chambers or bags 158a and 158b disposed in a confined housing 160 smaller than the combined volume of the two bags. A rigid plate or bar 162 is sandwiched between bags 158a and 158b and pivotably mounted to a heparin lock wall (not designated) via a pivot pin 164.

During a first half of a cycle of operation of systolic actuator 138, one chamber or bag 158a fills with intravenous fluid, while the other chamber or bag 158b empties its contents in a downstream direction towards the patient. During a second half of an operating cycle, the action is reversed so that bag 158b fills with intravenous fluid, while bag 158a empties. The filling of one bag 158a or 158b provides the impetus for forcing fluid from the other bag 158b or 158a.

Systolic actuator 138 extracts mechanical energy from the intravenous fluid flow and converts the extracted energy into a rocking of bar 162 about pivot pin 162. Bar 162 functions in part to actuate a pivoting or reversing valve 166 which controls the direction of fluid flow into and out of bags 158a and 158b.

Valve 166 is connected at a first port 168a to incoming intravenous line 146 and at a second port 168b to a downstream chamber 170 of heparin lock 137. Valve 166 is further coupled at third and fourth ports 168c and 168d, respectively, to bags 158a and 158b. Valve 166 is provided with a first arcuate channel 172 which connects intravenous line 146 to bag 158a in a first operating position of valve 166, illustrated in FIG. 7, and which connects bag 158a to downstream chamber 170 in a second operating position of valve 166. A second arcuate channel 174 in valve 166 couples bag 158b to downstream chamber 170 in the first operating position of the valve (FIG. 7), while in the second operating position (not illustrated) of valve 166, channel 174 links bag 158b to intravenous fluid supply 148 via line 146.

To pivot valve 166 through a 90° angle alternately in opposite directions, bar 162 is provided at one end with a leaf spring 176. During a beginning phase of an operating half-cycle of systolic actuator 138, leaf spring 176 engages a detent 178 connected to a housing wall (not designated) of heparin lock 137 and resiliently bends until bar 162 reaches a predetermined angled position, whereupon leaf spring 176 rapidly straightens and strikes one of two actuator arms 180a and 180b connected to valve 166. The striking of the actuator arm 180a or 180b causes valve 16 to pivot through 90°, thereby reversing the flowing of fluid in bags 158a and 158b.

At an end opposite leaf spring 176, bar 162 is provided with another leaf spring 182 which alternately strikes a pair of polymeric bellows 186a and 186b in housing 160. Bellows 186a and 86b are connected via ducts 188a and 188b to a polymeric pouch or air bladder 190. Pouch 190 is provided with perforations 192 or is air permeable or is provided with a porous plug (not shown) to slowly vent air fed to the pouch from bellows 186a and 186b.

Pouch 190 is disposed between two legs 194a and 194b of a leaf spring 196 having a sharp finger 194c which penetrates into chamber 170. As long as the flow of intravenous fluid through heparin lock 137 is sufficiently great, air pumped from bellows 186a and 186b in response to the pivoting of bar 162 keeps pouch 190 filled and finger 194c at a distance from a foil closure member 198 on a side of chamber 170 opposite pouch 190.

Foil member 198 serves to close a bladder or reservoir 200 pressurized via a spring member 202 and to prevent heparin in the reservoir from entering chamber 170. However, once the flow of air from bellows 186a and 186b falls below a predetermined rate, pouch 190 deflates and permits finger 194c of leaf spring 196 to puncture foil closure member 198. That breach of foil closure member 198 enables the forceful entry of heparin into chamber 170. One-way valve 156 prevents the inrushing heparin from flowing upstream.

Systolic actuator 138 is a flow sensing device in the form of a flow engine having a cycle of operation directly related to flow rate. Pouch 190, in cooperation with bellows 186a and 186b, serves to monitor and time the operating cycle of systolic actuator or engine 138. The operation of systolic actuator 138 and the monitoring of intravenous fluid flow along a flow path extending through intravenous line 146 and catheter 150 is accomplished while maintaining essentially steady flow to the patient.

It is to be noted that any number of positive displacement motor devices would achieve a function equivalent to that of systolic actuator 138. Systolic actuator 138 or an equivalent engine operates to divide the continuous intravenous fluid flow into a succession of aliquots of the intravenous liquid or solution. Watchdog timer 140, which includes pouch 190 cooperating with bellows 186a and 186b, monitors the operating cycles of the systolic actuator or engine 138. In the event that the timing is delayed by too great an amount, timer 140 causes the admission of heparin into chamber 170.

Systolic actuator 138 accumulates energy from the fluid steam and periodically releases the energy. Specifically, energy accumulated from the intravenous fluid flow by the action of bags 158a and 158b is stored in leaf spring 176 so that a substantial power burst of useful levels is available twice per cycle regardless of flow rate. The flow remains steady insofar as one chamber or bag 158a or 158b is emptying into the patient while the other is filling. The energy extracted by systolic actuator 138 from the intravenous flow is provided by opening a restrictor valve (not shown) at the intravenous supply more than otherwise necessary to achieved a desired flow rate.

The storage of flow energy in leaf spring 176 (and possibly 182) during each half cycle of operation of systolic actuator 138 ensures a proper reversal of valve 166 and a timely pumping of air to pouch 190 regardless of the flow rate along the intravenous flow path and, concomitantly, regardless of the speed with which the walls of bags 158a and 158b shift.

Figure 8:
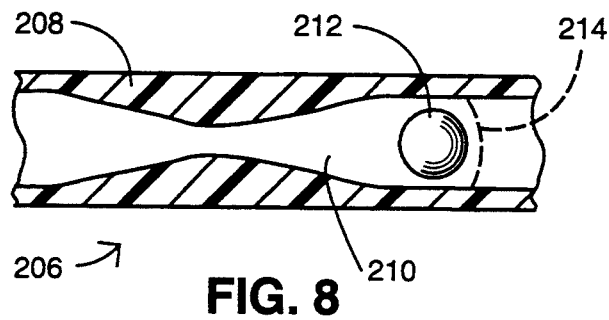
FIG. 8 is a schematic cross-sectional view of a one-way or blocking valve for use in automatic heparin locks described herein.

As illustrated in FIG. 8, a one-way blocking valve 206 for use in automatic heparin locks described hereinabove may take the form of a ball check valve without a spring. A wall 208 of a heparin lock chamber 210 bulges inwardly to provide a "jamming taper" in the reverse flow direction. Reverse flow jams the valve closed by virtue of either a compliant ball 212 or a resilient housing wall. After activation, excessive pressure beyond that normally available in an intravenous line would be required to dislodge ball from an narrowed canal formed by inwardly bulging wall. A cage or perforated wall 214 maintains ball 212 in place within a fixed distance from tapered wall portion 208.

Although the invention has been described in terms of particular embodiments and applications, one of ordinary skill in the art, in light of this teaching, can generate additional embodiments and modifications without departing from the spirit of or exceeding the scope of the claimed invention. For example, the geometry of the heparin containing chamber can take different forms, apparent to those skilled in the art. A plurality of heparin chambers may be connected via respective doors or valves to the channel in the body member.

As discussed hereinabove with reference to FIG. 1, flow sensitive device 14 may be sensitive to pressure. For example, a pressure sensor (not illustrated) may be placed in an intravenous flow line above a flow-regulating throttle valve (not illustrated) and operatively connected to a heparin valve at the catheter. In a simple form, the pressure sensor may take the form of a collapsible flexible envelope like pouch 190 disposed between the legs of a spring like spring 196, where the envelope or pouch is connected via a tube to the intravenous flow line above the flow-regulating throttle valve. Upon a diminution in pressure due to an exhaustion of the intravenous fluid supply, the envelope or pouch deflates and enables the spring to puncture a foil membrane, as described hereinabove with reference to FIG. 7.

It is to be noted that bellows 186a and 186b are advantageously provided with inlet and outlet check valves (not shown) so that the bellows function as air compressors. Alternatively, bellows or compressors 186a and 186b may be replaced with pistons and cylinders (not shown) also provided with inlet and outlet check valves. A bar or other rigid link may connect the pistons, or bellows/compressors 186a and 186b, to one another.

It is to be additionally noted that leaf springs 176 and 182 may be disposed at the same end of bar 162. Instead of the single centrally located detent 178, two detents (not shown) may be provided at opposite ends of the sweep of leaf spring 176, for increasing the period of energy accumulation and thereby enhancing efficiency and augmenting the force with which leaf spring 176 strikes actuator arms 180a and 180b. Moreover, actuator arms may be replaced by other equivalent impulse transference mechanisms, such as a rack and pinion arrangement (not illustrated) with a gear or pinion surrounding valve 166 and a rack which is struck by leaf spring 176.

Although heparin is the most widely used anticlotting agent, other equivalent compositions known to those skilled in the art may also or alternatively be used in the device and method in accordance with the present invention.

Accordingly, it is to be understood that the drawings and descriptions herein are proferred by way of example to facilitate comprehension of the invention and should not be construed to limit the scope thereof.

What is claimed is:

1. A method for use in an intravenous tube assembly, comprising the steps of:
   automatically dividing, into a succession of consecutive aliquots of liquid, a liquid flow along a fluid flow path extending through an intravenous catheter;
   automatically timing said consecutive aliquots to detect at least a partial cessation of liquid flow along said fluid flow path;
   upon detecting at least a partial cessation of liquid flow along said fluid flow path, automatically feeding an anticlotting agent to said fluid flow path; and
   upon feeding of said anticlotting agent to said fluid flow path, maintaining said anticlotting agent within a predetermined region of said fluid flow path.

2. The method defined in claim 1, further comprising the steps of automatically sensing said aliquots during motion thereof along said fluid flow path, said step of timing including the step of electronically monitoring said aliquots by generating an electrical signal upon the sensing of each consecutive aliquot.

3. The method defined in claim 2 wherein said aliquots constitute drops of liquid, said step of automatically sensing including the step of photoelectrically monitoring said drops.

4. The method defined in claim 2 wherein said step of feeding includes the steps of heating a meltable substance in a valve to open a valve member and thereby permit flow of said anticlotting agent from a reservoir to said fluid flow path.

5. The method defined in claim 1 wherein said step of automatically dividing includes the step of operating a fluid flow engine in said fluid flow path, said step of automatically timing including the step of monitoring the operating cycle of said fluid flow engine.

6. The method defined in claim 5 wherein said fluid flow engine is a systolic actuator having a pair of chambers, said step of automatically dividing including the step of alternately filling and emptying said chambers.

7. The method defined in claim 5 wherein said step of monitoring includes the step of using energy from said engine to pressurize a collapsible pouch, said step of feeding including the step of collapsing said pouch in response to a delay in the operation of said engine occasioned by a diminution of fluid flow along said flow path, said step of feeding further including the step of opening a pressurized reservoir of said anticlotting agent in response to said step of collapsing.

8. The method defined in claim 1, further comprising the step of automatically blocking communication between said catheter and an intravenous tube connected to said catheter.

9. The method defined in claim 1 wherein said step of automatically feeding comprises the step of automatically feeding a predetermined aliquot of said anticlotting agent to said fluid flow path.

10. The method defined in claim 1 wherein said step of automatically feeding includes the step of automatically opening a pressurized chamber containing said anticlotting agent.

11. The method defined in claim 1 wherein said anticlotting agent is heparin.

12. A method for use in an intravenous tube assembly, comprising the steps of:
   automatically accumulating energy from a flow of intravenous liquid along a fluid flow path extending through an intravenous catheter;
   automatically monitoring the rate of energy accumulation to detect at least a partial cessation of fluid flow along said flow path; and
   upon detecting at least a partial cessation of liquid flow along said fluid flow path, automatically feeding an anticlotting agent to said fluid flow path.

13. The method defined in claim 12 wherein said step of accumulating includes the step of supplying said energy to an energy storage device, further comprising the step of automatically releasing accumulated energy from said energy storage device.

14. The method defined in claim 13 wherein said energy storage device is a spring.

15. The method defined in claim 12 wherein said step of accumulating includes the step of driving a fluid flow engine disposed in said fluid flow path, said step of accumulating further including the step of transfering energy from said engine to an energy storage device.

16. The method defined in claim 15 wherein said engine is a systolic actuator having a pair of chambers, said step of driving including the step of alternately filling and emptying said chambers.

17. The method defined in claim 16 wherein said chambers are alternately expandable and contractible, said energy storage device being a leaf spring connected to a pivotably mounted bar disposed between said chambers.

18. A device for use with an intravenous catheter, comprising:

dividing means operatively connectable to said catheter for automatically dividing, into a succession of consecutive aliquots of liquid, a liquid flow along a fluid flow path extending through said catheter;

timing means operatively connected to said dividing means for automatically timing said consecutive aliquots to detect at least a partial cessation of liquid flow along said fluid flow path; and feeder means operatively connected to said timing means and couplable to said catheter for automatically feeding an anticlotting agent to said fluid flow path upon a detection by said timing means of at least a partial cessation of liquid flow along said fluid flow path; and holding means adapted to be connected to the catheter and connected to said feeder means for maintaining said anticlotting agent within a predetermined region of said fluid flow path upon feeding of said anticlotting agent to said fluid flow path by said feeder means.

19. The device defined in claim 18 wherein said dividing means includes a fluid flow engine, said timing means including monitoring means operatively connected to said engine for monitoring an operating cycle thereof.

20. The device defined in claim 19 wherein said fluid flow engine is a systolic actuator having a pair of chambers, said dividing means including means operatively connected to said actuator for filling one of said chambers with liquid from said fluid flow path while emptying another of said chambers of liquid during a half cycle of operation of said systolic actuator.

21. The device defined in claim 20 wherein said monitoring means includes a collapsible pouch having an air outlet, said systolic actuator including pressurization means operatively connected to said pouch for supplying a pressurizing air charge to said pouch during a cycle of operation of said systolic actuator, said feeder means including opening means operatively connected to said pouch for opening communication between said fluid flow path and a storage chamber containing said anticlotting agent.

22. The device defined in claim 21 wherein said feeder means further includes a spring member with said opening means, said opening means including a pointed portion of said spring member, said pouch being disposed between two legs of said spring member, whereby said pointed portion punctures a closure member to open said storage chamber upon a collapse of said pouch.

23. The device defined in claim 21 wherein said pressurization means includes a pump operatively coupled to said chambers for providing air to said pouch in response to periodic filling and emptying of said chambers.

24. The device defined in claim 20 wherein said dividing means further includes means for reversing operation of said systolic actuator to fill said another of said chambers while emptying said one of said chambers.

25. The device defined in claim 18, further comprising a pressurized chamber containing a predetermined amount of said anticlotting agent, said feeder means including means for opening communication between said chamber and said fluid flow path.

26. The device defined in claim 18, further comprising means connected to said dividing means for automatically blocking reverse flow of fluid along said flow path from said catheter to an intravenous tube upon an actuation of said feeder means.

27. A device for use with an intravenous catheter, comprising:

energy accumulation means operatively connectable to said catheter for automatically accumulating energy from a flow of intravenous liquid along a fluid flow path extending through said catheter;

monitoring means operatively connected to said energy accumulation means for automatically monitoring the rate of energy accumulation to detect at least a partial cessation of fluid flow along said flow path; and feeder means operatively connected to said monitoring means and couplable to said catheter for automatically feeding an anticlotting agent to said fluid flow path upon a detection by said monitoring means of at least a partial cessation of liquid flow along said fluid flow path.

28. The device defined in claim 27 wherein said monitoring means includes a spring and means operatively coupled with said spring for maintaining said spring in an energy bearing configuration, said spring including a pair of substantially parallel legs connected at one end to one another, said means for maintaining including a pouch disposed between said legs, said monitoring means further comprising means for pressurizing said pouch in response to liquid flow along said fluid flow path.

29. The device defined in claim 28 wherein said feeder means includes opening means operatively connected to said pouch for opening communication between said fluid flow path and a storage chamber containing said anticlotting agent.

30. The device defined in claim 29 wherein said feeder means further includes a spring member with said opening means, said opening means including a pointed portion of said spring member, said pouch being disposed between two legs of said spring member, whereby said pointed portion punctures a closure member to open said storage chamber upon a collapse of said pouch.

31. The device defined in claim 30 wherein said pouch is provided with an outlet, whereby said pouch automatically depressurizes under pressure by said legs of said spring in the absence of pressurization.

32. The device defined in claim 30 wherein said energy accumulation means includes a systolic actuator having a pair of chambers connectable to said flow path and further includes means operatively connected to said actuator for filling one of said chambers with liquid from said fluid flow path while emptying another of said chambers of liquid during a half cycle of operation of said systolic actuator, said means for pressurizing including a bellows type pump operatively connected to said systolic actuator for activation thereby in response to flow of fluid along said flow path.

33. The device defined in claim 27 wherein said energy accumulation means includes a flow engine connectable to said flow path.

34. The device defined in claim 31 wherein said flow engine is a systolic actuator having a pair of chambers, said accumulation means including means operatively connected to said actuator for filling one of said chambers with liquid from said fluid flow path while emptying another of said chambers of liquid during a half cycle of operation of said systolic actuator.

35. The device defined in claim 34 wherein said accumulation means further includes means for reversing operation of said systolic actuator to fill said another of said chambers while emptying said one of said chambers.

* * * * *